(12) United States Patent
Burch

(10) Patent No.: US 12,315,625 B2
(45) Date of Patent: May 27, 2025

(54) ARTIFICIAL INTELLIGENCE ASSISTED DYNAMIC MEDICAL APPOINTMENT SCHEDULING

(71) Applicant: Lupen Corporation, Harbor Springs, MI (US)

(72) Inventor: Todd C. Burch, Harbor Springs, MI (US)

(73) Assignee: Lupen Corporation, Harbor Springs, MI (US)

( * ) Notice: Subject to any disclaimer, the term of this patent is extended or adjusted under 35 U.S.C. 154(b) by 0 days.

(21) Appl. No.: 18/783,733

(22) Filed: Jul. 25, 2024

(65) Prior Publication Data

US 2025/0046438 A1 Feb. 6, 2025

Related U.S. Application Data

(60) Provisional application No. 63/517,037, filed on Aug. 1, 2023.

(51) Int. Cl.
*G06Q 10/00* (2023.01)
*G06Q 10/1093* (2023.01)
*G16H 40/00* (2018.01)
*G16H 40/20* (2018.01)

(52) U.S. Cl.
CPC ......... *G16H 40/20* (2018.01); *G06Q 10/1095* (2013.01)

(58) Field of Classification Search
CPC .............................. G16H 40/00; G06Q 10/00
USPC ........................................................ 705/7.19
See application file for complete search history.

(56) References Cited

U.S. PATENT DOCUMENTS

| | | | |
|---|---|---|---|
| 2014/0058739 A1* | 2/2014 | Guerra-Mondragon Gonzalez | G16H 40/20 705/2 |
| 2016/0379173 A1* | 12/2016 | Karnati | G06Q 30/0235 705/7.19 |
| 2022/0262468 A1* | 8/2022 | AlQabandi | G16H 10/60 |
| 2022/0406441 A1* | 12/2022 | Linares | G16H 50/70 |
| 2023/0005607 A1* | 1/2023 | Kogan | G16H 50/20 |

* cited by examiner

*Primary Examiner* — Mustafa Iqbal
(74) *Attorney, Agent, or Firm* — Honigman LLP

(57) ABSTRACT

A method includes receiving, from a person via a user interface, a request to schedule a medical appointment for a patient, and identifying, using a scheduling module, one or more available appointment slots for scheduling of the medical appointment. For each particular available appointment slot of the one or more available appointment slots, the method includes determining, using a load-leveling model, a corresponding price. The method also includes presenting, in the user interface for the person, the one or more available appointment slots and the corresponding prices, receiving, at the scheduling module, from the person via the user interface, a selection of a selected appointment slot of the one or more available appointment slots, and allocating the corresponding price for the selected appointment slot to an account associated with the patient, and scheduling, using the scheduling module, the patient for the medical appointment in the selected appointment slot.

26 Claims, 6 Drawing Sheets

FIG. 2

| Level | IP Benefits Bed Occupancy | IP Benefits Food | IP Benefits - ED Boarding Priority Bed Assignment | IP Benefits - Discharge | IP Benefits - Rounding |
|---|---|---|---|---|---|
| Diamond | Guaranteed Single Occupancy | Preferred Menu & Dietician consult Included | Priority 1 | Navigator for care coordination | CEO / CMO / Foundation CEO |
| Platinum | Single Occupancy Priority 1 | Preferred Menu Included & Dietician consult for Fee | Priority 2 | Early Discharge Priority 1 - Navigator at stratified cost | Executive Rounds / Foundation Staff |
| Gold | Single Occupancy Priority 2 | Preferred Menu & Dietician consult for added fee | Priority 3 | Early Discharge Priority 2 - Navigator at stratified cost | Unit Leader Priority 1 |
| Silver | Single Occupancy Priority 3 | Preferred Menu & Dietician consult for added fee | Priority 4 | Early Discharge Priority 3 - Navigator at stratified cost | Unit Leader Priority 2 |
| Member | Single Occupancy Priority 4 | Preferred Menu & Dietician consult for added fee | Priority 5 | Discharge Priority 4 - Navigator at stratified cost | Unit Leader Priority 3 |
| Non-member | Single Occupancy Priority 5 | Preferred Menu at higher rate | Priority 6 | Discharge Priority 5 - Navigator at stratified cost | Unit Leader Priority 4 |
| Benefits to Health System | Upcharge for Private Room | Reduces Options on Standard Menu to 2 items | | Increases likelihood of Follow up and decreased readmission | Focuses rounding on highest value patients to the system |
| | | Incentivizes Paying Extra for better food | | Makes navigators a profit center instead of a cost center | |

FIG. 3

ARTIFICIAL INTELLIGENCE ASSISTED DYNAMIC MEDICAL APPOINTMENT SCHEDULING

CROSS REFERENCE TO RELATED APPLICATIONS

This U.S. patent application claims priority under 35 U.S.C. § 119 (e) to U.S. Provisional Patent Application 63/517,037, filed on Aug. 1, 2023. The disclosure of this prior application is considered part of the disclosure of this application and is hereby incorporated by reference in its entirety.

BACKGROUND

Today, in service industries (e.g., the healthcare industry, the veterinary industry, the home repair service industry, and the equipment repair services industry, to name just a few), the providers of services manually allocate their resources in an effort to balance their schedule with the perceived needs of a customer (e.g., patient).

SUMMARY

One aspect of the disclosure provides a computer-implemented method that, when executed on data processing hardware, causes the data processing hardware to perform operations. The operations include receiving, from a person via a user interface, a request to schedule a medical appointment for a patient, and identifying, using a scheduling module, one or more available appointment slots for scheduling of the medical appointment. The operations also include, for each particular available appointment slot of the one or more available appointment slots, determining, using a load-leveling model, a corresponding price. The load-leveling model trained by a training process that trains the load-leveling model by obtaining training data including historical data representing a plurality of past medical appointments, and training the load-leveling model, using the training data, to determine a corresponding price for a particular appointment slot to achieve a target utilization rate for the particular appointment slot. The operations further include presenting, in the user interface for the person, the one or more available appointment slots and the corresponding prices, receiving, at the scheduling module, from the person via the user interface, a selection of a selected appointment slot of the one or more available appointment slots, allocating the corresponding price for the selected appointment slot to an account associated with the patient, and scheduling, using the scheduling module, the patient for the medical appointment in the selected appointment slot.

Implementations of the disclosure may include one or more of the following optional features. In some implementations, at least one of the available appointment slots for scheduling of the requested medical appointment includes corresponding available appointments slots for one or more medical providers that can perform the medical appointment; determining the corresponding price for the at least one of the available appointment slots includes determining a corresponding price for each of the one or more medical providers for the at least one the available appointment slots; and presenting, in the user interface for the person, the one or more available appointment slots and the corresponding prices includes presenting the corresponding available appointment slots for the one or more medical providers and the corresponding price for each of the one or more medical providers for the at least one of the available appointment slots.

In some examples, the load-leveling model includes a trained machine learning (ML) model. In some examples, the historical data includes, for each past appointment of the plurality of past appointments, at least one of a date, a day of a week, a day of a month, a month of a year, a scheduled start time, an actual start time, a duration, a current procedural terminology (CPT) code, a procedure description, a practitioner identifier, an equipment identifier, a location identifier, a room identifier, or a surcharge amount. The historical data may represent past appointments for a plurality of medical providers.

In some implementations, the training process trains the load-leveling model, using the training data, to increase a revenue associated with a particular appointment slot. In some examples, the training process trains the load-leveling model to determine the corresponding price based on loyalty program information for the patient. In some implementations, allocating the corresponding price for the selected appointment slot to the account associated with the patient includes deducting points from a loyalty program account associated with the patient.

In some examples, the training process trains the load-leveling model to determine the corresponding price for an available appointment slot based on a rating for a medical provider. The rating for the medical provider may include at least one of an overall rating, a patient satisfaction score, a volume, a duration of service rating, an on-time start rating, or a case mix rating. In some implementations, the operations also include determining, using a ratings machine learning (ML) model, the rating for the medical provider, wherein a second training process trains the rating ML model by obtaining records from an electronic health records (EHR) system associated with a plurality of medical providers, and training the rating ML model, using the records, to determine one or more ratings for each of the plurality of medical providers. In some examples, the second training process obtains current ratings information for each of the plurality of medical providers, and trains the rating ML model, using the records and the current ratings information, to determine the one or more ratings for each of the plurality of medical providers.

In some implementations, presenting, in the user interface for the person, the one or more available appointment slots and the corresponding prices includes presenting a schedule, wherein the schedule includes each available appointment slot the corresponding price. In some examples, the prices include a surcharge that is charged to the patient, wherein the surcharge is separate from an amount charged to an insurer for the medical appointment.

Another aspect of the disclosure provides a system that includes data processing hardware and memory hardware storing instructions that, when executed on the data processing hardware, cause the data processing hardware to perform operations. The operations include receiving, from a person via a user interface, a request to schedule a medical appointment for a patient, and identifying, using a scheduling module, one or more available appointment slots for scheduling of the medical appointment. The operations also include, for each particular available appointment slot of the one or more available appointment slots, determining, using a load-leveling model, a corresponding price. The load-leveling model trained by a training process that trains the load-leveling model by obtaining training data including historical data representing a plurality of past medical appointments, and training the load-leveling model, using the training data, to determine a corresponding price for a particular appointment slot to achieve a target utilization rate for the particular appointment slot. The operations further include presenting, in the user interface for the person, the one or more available appointment slots and the corresponding prices, receiving, at the scheduling module, from the person via the user interface, a selection of a selected appointment slot of the one or more available appointment slots, allocating the corresponding price for the selected appointment slot to an account associated with the patient, and scheduling, using the scheduling module, the patient for the medical appointment in the selected appointment slot.

Implementations of the disclosure may include one or more of the following optional features. In some implementations, at least one of the available appointment slots for scheduling of the requested medical appointment includes corresponding available appointments slots for one or more medical providers that can perform the medical appointment; determining the corresponding price for the at least one of the available appointment slots includes determining a corresponding price for each of the one or more medical providers for the at least one the available appointment slots; and presenting, in the user interface for the person, the one or more available appointment slots and the corresponding prices includes presenting the corresponding available appointment slots for the one or more medical providers and the corresponding price for each of the one or more medical providers for the at least one of the available appointment slots.

In some examples, the load-leveling model includes a trained machine learning (ML) model. In some examples, the historical data includes, for each past appointment of the plurality of past appointments, at least one of a date, a day of a week, a day of a month, a month of a year, a scheduled start time, an actual start time, a duration, a current procedural terminology (CPT) code, a procedure description, a practitioner identifier, an equipment identifier, a location identifier, a room identifier, or a surcharge amount. The historical data may represent past appointments for a plurality of medical providers.

In some implementations, the training process trains the load-leveling model, using the training data, to increase a revenue associated with a particular appointment slot. In some examples, the training process trains the load-leveling model to determine the corresponding price based on loyalty program information for the patient. In some implementations, allocating the corresponding price for the selected appointment slot to the account associated with the patient includes deducting points from a loyalty program account associated with the patient.

In some examples, the training process trains the load-leveling model to determine the corresponding price for an available appointment slot based on a rating for a medical provider. The rating for the medical provider may include at least one of an overall rating, a patient satisfaction score, a volume, a duration of service rating, an on-time start rating, or a case mix rating. In some implementations, the operations also include determining, using a ratings machine learning (ML) model, the rating for the medical provider, wherein a second training process trains the rating ML model by obtaining records from an electronic health records (EHR) system associated with a plurality of medical providers, and training the rating ML model, using the records, to determine one or more ratings for each of the plurality of medical providers. In some examples, the second training process obtains current ratings information for each of the plurality of medical providers, and trains the rating ML model, using the records and the current ratings information, to determine the one or more ratings for each of the plurality of medical providers.

In some implementations, presenting, in the user interface for the person, the one or more available appointment slots and the corresponding prices includes presenting a schedule, wherein the schedule includes each available appointment slot the corresponding price. In some examples, the prices includes a surcharge that is charged to the patient, wherein the surcharge is separate from an amount charged to an insurer for the medical appointment.

The details of one or more implementations of the disclosure are set forth in the accompanying drawings and the description below. Other aspects, features, and advantages will be apparent from the description and drawings, and from the claims.

DESCRIPTION OF DRAWINGS

FIG. 2 illustrates an example scheduling user interface for presenting one or more available appointments slots;

FIG. 3 is a table of example loyalty program benefits.

Like reference symbols in the various drawings indicate like elements.

DETAILED DESCRIPTION

Figure 1:
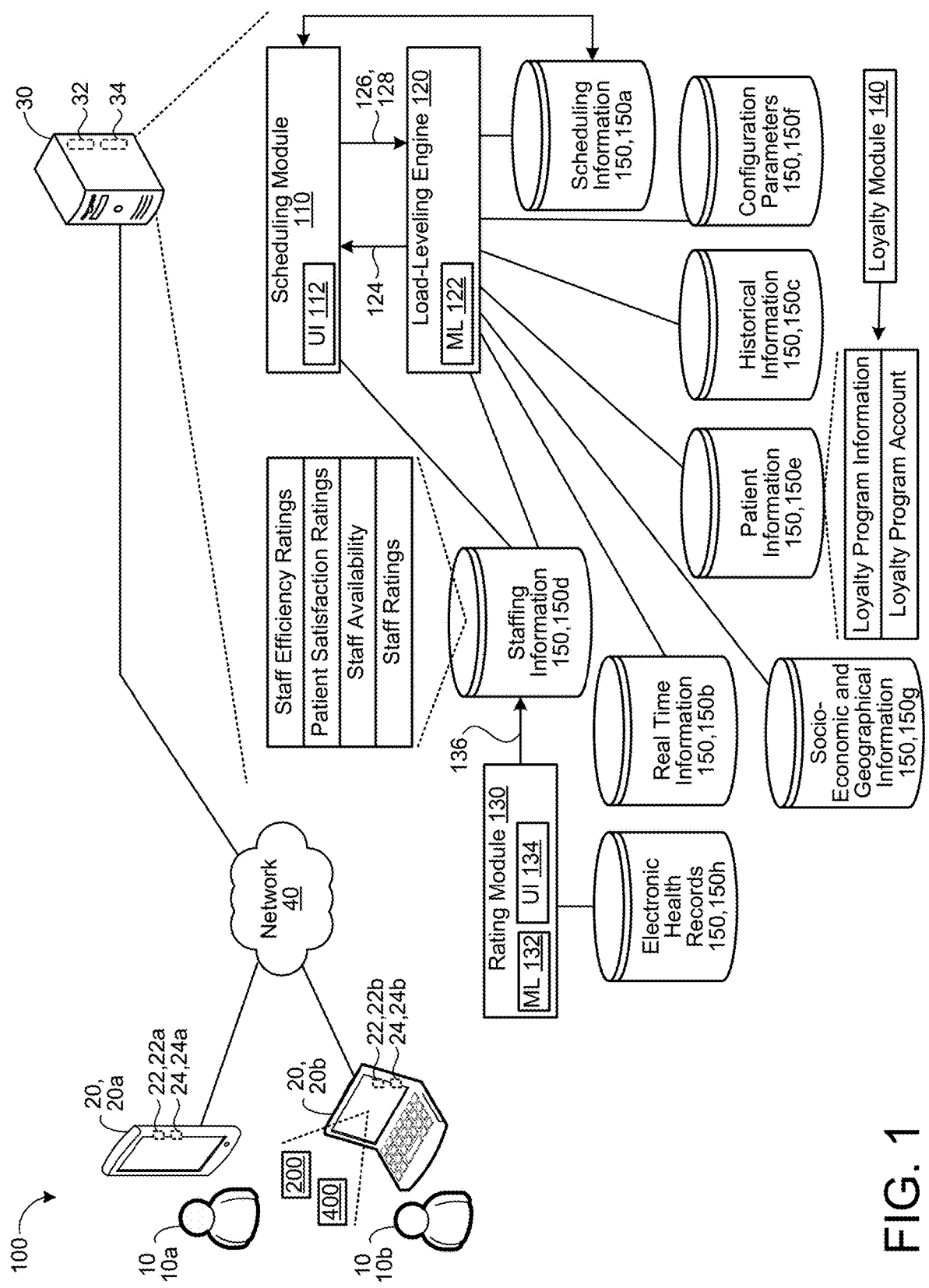
FIG. 1 is a schematic view of an example artificial intelligence (AI) assisted dynamic medical appointment scheduling.

Today, in service industries (e.g., the healthcare industry, the veterinary industry, the home repair service industry, and the equipment repair services industry, to name just a few), the providers of services manually allocate their resources in an effort to balance their schedule with the perceived needs of a customer (e.g., patient). However, such balancing does not take into account the value of the customer's time, and the value of certain peak and trough times for a given day, week, or month. Therefore, there is a need for load-leveling of appointment slots to balance utilization of appointment slots, increase revenue, improve client satisfaction, and/or improve staffing satisfaction.

Implementations disclosed herein dynamically balance utilization of appointment slots and monetize the value of appointment slots as a function of time-of-day and day-of-week relative to a value a customer may place on appointment slots based upon their personal schedule and/or preferences, provider scheduling, staffing constraints, historical scheduling data, etc. It has been advantageously discovered that a service provider may use artificial intelligence (AI) to determine when to charge more (e.g., charge a premium) or when to charge less (e.g., offer a discount) for particular appointment slots. For example, implementations disclosed herein may process historical data of a service provider, using AI, to individually determine the dynamic monetary value of each appointment slot. The AI may allow the service provider to balance utilization of appointment increase the monetary value of each appointment slot while also load-leveling across the service provider's schedule to more efficiently utilize the service provider's resources (e.g., staff, equipment, and/or facilities). For example, slot A may be worth X, slot B may be worth X+K and slot C may be worth X−M. Therefore, disclosed implementations may represent a substantial financial benefit to a service provider. For instance, disclosed implementations may empower customers to express their urgency and desires while letting the service provider fit into the customer's schedule and while increasing the service provider's overall schedule utilization and revenue. If the service is one that must be delivered remotely, such as a plumber going to a distant house, the AI may also take into account the distance between adjacent appointments and adjust pricing accordingly. Accordingly, disclosed embodiments may enable a service provider to create a new revenue stream by increasing the value of high-demand appointment slots, while simultaneously realizing load balancing across appointment slots for staffing or resource purposes.

For clarity of explanation, disclosed embodiments will be described with reference to medical appointments. However, persons of ordinary skill in the art will readily appreciate that disclosed embodiments are also applicable to any other service industry. Moreover, the term medical provider will be used herein to refer to any person that provides or performs any type of medical service, procedure, test, etc. Example medical providers include, but are not limited to, a doctor, a dentist, a nurse, a technician, and a staff member. Furthermore, the term medical resource will be used herein to refer to any resource used to provide or perform any type of medical service, procedure, test, etc. Example medical resources include, but are not limited to, a campus, a facility, an office, a room, and a piece of equipment.

FIG. 1 is a diagram of an example of an artificial intelligence (AI) assisted dynamic medical appointment scheduling system 100 for, among other purposes, dynamically determining pricing for available appointment slots for a medical appointment for load leveling. In the illustrated example, a request for the medical appointment is received from a person 10, 10*a-n*, such as a patient 10*a*, a representative for the patient 10*a*, or a representative 10*b* of a medical provider for the requested medical appointment. The medical appointment request may be received via, or from, any number and/or type(s) of user devices 20, 20*a-n*. The user devices 20 may correspond to any computing device associated with a person 10. Some examples of user devices 20 include, but are not limited to, mobile devices (e.g., mobile phones, a smartphone 20*a*, tablets, laptops, etc.), computers (e.g., a laptop computer 20*b*), wearable devices (e.g., smart watches), smart appliances, Internet of things (IoT) devices, vehicle infotainment systems, smart displays, smart speakers, etc. The user devices 20 each include respective data processing hardware 22, 22*a-n* and respective memory hardware 24, 24*a-n* in communication with the data processing hardware 22. Here, the memory hardware 24 stores instructions that, when executed by the data processing hardware 22, cause the data processing hardware 22 to perform one or more operations, such as those disclosed herein.

To schedule medical appointments and dynamically determine pricing for requested medical appointments, the AI assisted dynamic medical appointment scheduling system 100 includes a computing device 30 (e.g., a local server associated with one or more medical providers, a remote server of a distributed system executing in a cloud-computing environment, etc.) in communication with the user devices 20 via any number and/or type(s) of public and/or private communication network(s) 40. The computing device 30 includes data processing hardware 32, and memory hardware 34 in communication with the data processing hardware 32. The memory hardware 34 stores instructions that, when executed by the data processing hardware 32, cause the data processing hardware 32 to perform one or more operations, such as those disclosed herein.

In the illustrated example, the computing device 30 executes a scheduling module 110, and a load-leveling engine 120. Alternatively or additionally, a user device 20 associated with a representative 10*b* of a medical provider may execute the scheduling module 110, and/or the load-leveling engine 120. The scheduling module 110 executes, among possibly other modules, a scheduling user interface (UI) module 112 configured to provide, on a display of a user device 20, a scheduling UI 200 (e.g., see FIG. 2) that enables a representative of a medical provider to interact with a scheduling information datastore 150, 150*a* to see an appointment schedule of the medical provider, identify available medical appointment slots 128, determine dynamic pre-appointment slot prices 124 for appointment slots 128, schedule appointments, update appointments, change appointments, cancel appointments, etc. In some implementations, the scheduling UI module 112 may also enable a patient 10*a* or their representative to themselves obtain dynamic per-appointment slot prices, schedule, change, update, and/or cancel their appointments. In some examples, the scheduling information datastore 150*a* stores data that represents, for each appointment slot of a medical provider, whether a patient 10*a* has been scheduled in appointment slot, a patient 10*a* identifier, what medical resources are associated with the scheduled appointment, etc. The scheduling information datastore 150*a* may also store data that represents the scheduling of each medical resource of a medical provider.

The load-leveling engine 120 may be, or include, a portion of a memory unit (e.g., the memory hardware 34) configured to store software, and machine- or computer-readable instructions that, when executed by a processing unit (e.g., the data processing hardware 32), cause the load-leveling engine 120 to determine dynamic per-appointment slot pricing for a requested medical appointment. In the illustrated example, the load-leveling engine 120 dynamically determines prices for medical appointments using a trained load-leveling machine learning (ML) model 122. In particular, the load-leveling engine 120 dynamically determines appointment slot prices 124 by inputting to the load-leveling ML model 122 input data 126 that may include data from, one or more of, the scheduling information datastore 150*a* (e.g., available appointment time slots 128), a real time information datastore 150, 150*b*, a historical information datastore 150, 150*c*, a staffing information datastore 150, 150*d*, a patient information datastore 150, 150*e*, a configuration parameter datastore 150, 150*f*, and/or a socio-economic and geographical information datastore 150, 150*g*. The dynamic pricing for a particular medical appointment slot may include a premium, fee, upcharge, or surcharge that will be charged to the patient 10*a*. Here, the premium, fee, upcharge, or surcharge may have a positive or negative value as, for example, the load-leveling ML model 122 load levels a medical provider's schedule and medical resources. For example, a patient 10*a* might be charged a premium, fee, upcharge, or surcharge when they select a more popular or convenient appointment slot, or might be credited a discount when they select a less popular or more inconvenient appointment slot. Here, the premium, fee, upcharge, or surcharge is paid by the patient 10a, and is separate from any amount billed to an insurer for the particular medical appointment. The load-leveling ML model 122 may be, or include, a portion of a memory unit (e.g., the memory hardware 34) configured to store software, and machine- or computer-readable instructions that, when executed by a processing unit (e.g., the data processing hardware 32, a graphics processing unit (GPU), a tensor processing unit (TPU), etc.), cause the load-leveling ML model 122 to dynamically determine prices for medical appointments.

In some examples, the real time information datastore 150b stores data that represents a patient's schedule (e.g., provided by a patient 10a to a staff member via a telephone call), a current call volume of a medical provider, and/or a call-to-appointment conversion ratio.

In some examples, the historical information datastore 150c stores data that represents, for each appointment slot and/or medical resource of a medical provider, a no show rate, a cancellation rate, cancellation reason codes, and/or cancellations by day/time. The historical information datastore 150c may also contain data that represents utilization (e.g., a mean, a median, a minimum and/or a maximum utilization) by appointment slot, medical provider, and/or medical resource. The historical information datastore 150c also stores historical data representing a plurality of past medical appointments. Here, the historical data includes, for each of a plurality of past appointments, one or more of a date, a day of a week, a day of a month, a month of a year, a scheduled start time, an actual start time, a duration, a current procedural terminology (CPT) code, a procedure description, a medical provider identifier, an equipment identifier, a location identifier, a room identifier, or a surcharge amount. In some examples, the historical information datastore 150c stores data for a plurality of medical providers, medical facilities, etc.

In some examples, the staffing information datastore 150d stores data that represents full-time equivalents (FTEs), worked FTEs, scheduled hours, regular work days, normal days off, holidays, vacations, sick leave, etc. In some implementations, the staffing information datastore 150d may also store data that represents staff efficiency ratings, patient 10a satisfaction ratings and/or reviews, staff availability, staff ratings by modality, etc.

In some examples, the patient information datastore 150e stores data that represents name, address, contact information, insurance information, scheduling preferences, work schedule, payment account information, loyalty program information, loyalty program account information, etc.

In some examples, the configuration parameters datastore 150f stores data that represents parameters that control pricing (e.g., a minimum price, a maximum price, etc.) and/or load-leveling (e.g., a target utilization rate).

In some examples, the socio-economic and geographical information datastore 150g stores data that presents the socio-economic and/or geographical differences that exist across different medical providers. For example, different zip codes may have variations in median income and, thus, persons living in one zip code may be more sensitive to price than persons living in a different zip code.

In some implementations, a training process trains the load-leveling ML model 122, based on at least the historical information 150c, to dynamically price available appointment slots to achieve a target utilization rate of, and/or to increase a revenue associated with, each available appointment slots. An example target utilization rate is 75% to 85%. Here, slot utilization may be for a particular treatment, a particular medical provider, a particular medical resource, etc. In some examples, the target utilization rate is selected to be lower to accommodate emergency add-ons (e.g., at 65%), and/or selected to be higher when appointment slots are associated with historically higher no show or cancellation rates. In some examples, the price for an appointment slot is constrained to be between a pre-configured minimum (e.g., zero) and a pre-configured maximum (e.g., $125). Based on the scheduling information 150a and the historical information 150c, the load-leveling ML model 122 may be trained to assign prices to each appointment slot to achieve the target utilization rate and an average price per slot. For example, the load-leveling ML model 122 may be trained to determine discounts such as:

a 100% discount for slots with less than a 35% historical utilization a 70% discount for slots with between 35% and 50% historical utilization a 50% discount for slots with between 50% and 65% historical utilization a 30% discount for slots with between 65% and 75% historical utilization a 0% discount for slots with between 75% and 85% historical utilization a 5% upcharge for slots with between 85% and 95% historical utilization a 10% upcharge for slots with between 95% and 105% historical utilization a 25% upcharge for slots with greater than 105% historical utilization In some implementations, a training process also trains the load-leveling ML model 122, based on the socio-economic and geographical information 150g, to dynamically price available appointment slots to achieve a target utilization rate for each available appointment slots such that the dynamically determined price differs between different zip codes.

Of particular note is that the load-leveling ML model 122 may be trained using historical information 150c collected for a plurality of treatments, medical providers, medical resources, etc. Also of particular note is that the load-leveling ML model 122 determines pricing on an individual treatment, medical provider, medical resource, etc. basis. For example, five doctors in the same clinic may have five different prices for their Tuesday at 3:00 pm appointment slot based on their historical utilization of Tuesday's at 3:00 pm. This creates a unique price structure for each treatment, medical provider, and medical resource at a particular time. Moreover, because the load-leveling ML model 122 is trained using historical information 150c collected for a plurality of treatments, medical providers, medical resources, etc., the load-leveling ML model 122 can, for example, determine historical utilization of MRI machines across a wide range of similar locations providing similar services and refine the costs for a particular location based on their unique schedule structure, complexity of care, and customer demand.

Additionally or alternatively, the load-leveling ML model 122 may be trained to determine that particular appointment slots are consistently being over utilized even when premiums are being charged for those appointment slots, and determine additional work and/or wage premiums that may be offered to staff to ensure adequate staffing for those particular high-demand appointment slots.

Additionally or alternatively, in some implementations, the load-leveling ML model 122 is trained to allow a person 10 to pick the particular medical provider who will handle their requested medical appointment. For example, the scheduling UI module 112 may be configured to display ratings, reviews, and/or compensation rates for a medical provider they are considering picking. Here, ratings and reviews may be for each medical provider basis and/or on a treatment modality by treatment modality basis. Such a scheduling UI module 112 allows the person 10 to feel as comfortable as possible with the medical provider who will handle their requested medical appointment. This may also incentivize great customer service in every interaction as they may be rated by any particular patient 10a, and because such reviews may be seen by other patients. Following the service, the patient 10a may be provided an opportunity to rate the medical provider that provided their service, and those ratings may be reflected in the medical provider's future compensation. In some implementations, medical provider ratings may be solicited and received via text messaging. In some examples, when a person 10 selects a particular medical provider for a selected appointment slot 128 and their requested medical appointment is scheduled, the scheduling module 110 may also update the staffing information datastore 150d to represent that the particular medical provider is booked for the selected appointment slot 128.

Figure 2:
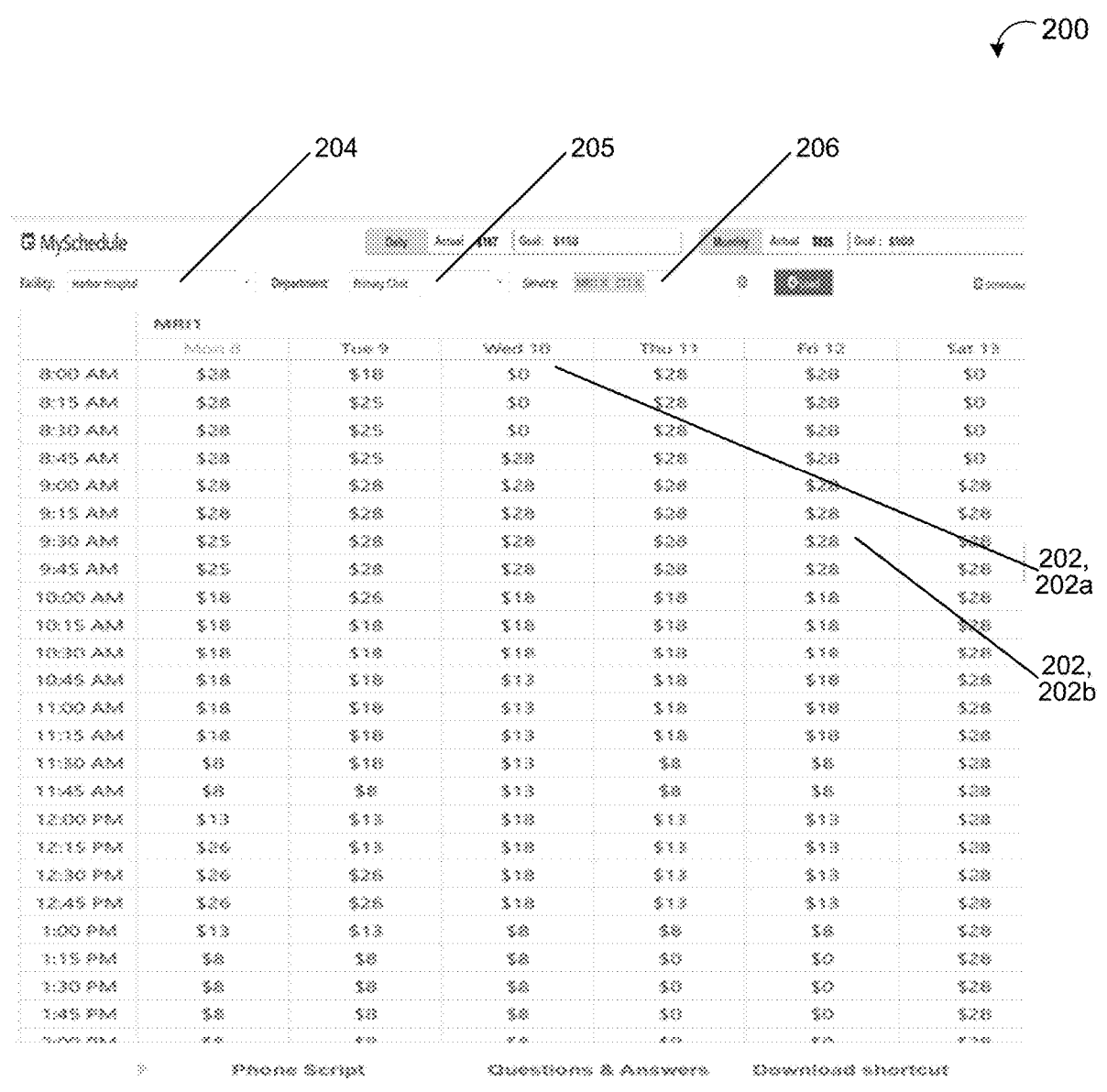

In some implementations, the training process also trains the load-leveling ML model 122 to dynamically price available appointment slots for a plurality of different medical providers for a particular medical appointment. For example, the scheduling module 110 may identify one or more available appointment slots for scheduling of the particular medical appointment, where at least one of the available appointment slots for scheduling of the requested medical appointment includes corresponding available appointments slots for one or more medical providers that can perform the medical appointment. The load-leveling engine 120 can then determine a corresponding price for each of the one or more medical providers for the at least one the available appointment slots. Finally, the scheduling UI module 112 presents the one or more available appointment slots and the corresponding prices includes presenting the corresponding available appointment slots for the one or more medical providers and the corresponding price for each of the one or more medical providers for the at least one of the available appointment slots FIG. 2 illustrates an example scheduling UI 200 that may be presented by the schedule UI module 112 for presenting one or more available appointments slots and corresponding prices. The scheduling UI 200 may be, for example, a web-based interface. The example scheduling user interface 200 includes a plurality of entries 202, 202a-n. Each entry 202 represents a corresponding price determined by the load-leveling ML model 122 for a corresponding appointment slot at a particular day and time. For example, an entry 202a indicates that scheduling an appointment at 8:00 am on Wednesday will not incur an additional cost, while an entry 202b indicates that scheduling an appointment at 9:30 am on Friday will have an additional cost of $28. Here, the cost is associated with a particular facility 204 a particular department 205, for a particular service 206. In this example, the scheduling user interface 200 includes drop-down boxes 204-206 that allow a user to select the particular facility 204, the particular department 205, and the particular service 206.

Returning to FIG. 1, in some examples, work scheduling and/or wage information may be used to convert medical providers to contractors, and pay them for each service they provide as opposed to paying them for hours worked. This may effectively be used to pay medical providers for value creation instead of just paying for time. This may be used, in turn, to convert conventional fixed salaries or hourly rate into a demand-based variable expense. In some examples, the load-leveling ML model 122 takes into account a medical provider's efficiency, satisfaction ratings, and/or peer group performance to adjust compensation periodically for the medical provider. In some examples, patients may contribute directly to the medical provider's satisfaction score via their user device 20. Moreover, in some implementations, a patient 10a may be charged a "per instance fee" equivalent to the rate that a medical provider would have received per hour prorated to the duration of the service, which may be part of the appointment slot prices 124 that the patient 10a is quoted. For example, if a medical provider has an hourly rate of $38 and a service takes 30 minutes, a 5 star rated medical provider may receive $24 for the 30 minute service paid by the patient 10a. This is the equivalent of $48 per hour which is the equivalent of a 26% premium for a highly rated medical provider. The medical provider is certainly going to be happy to earn more, which will incentivize them to create better experiences for each customer. The medical provider may also be happier because their fixed hourly staffing expense converts to a variable expense that is paid in whole or in part by the patient 10a. Additionally or alternatively, the model may take into account historical efficiency compared to current performance and weight the output accordingly. This would be revolutionary in the medical industry, and may be useful to medical providers wanting to increase customer satisfaction, decrease costs, and/or increase margins in the face of increasing financial and/or insurance constraints.

Additionally, in some implementations, the load-leveling ML model 122 is trained to dynamically price available appointment slots based on a loyalty program information 150e. In some implementations, a loyalty program is similar to a banking account that a patient 10a has with a medical provider. Here, the patient 10a earns points in their account for swiping a healthcare system branded credit card, using services of the medical provider, participating in activities like taking health questionnaire's, uploading their smartwatch data, etc. All of this provides data that the medical provider may find helpful in retaining the patient 10a as a customer. The patient 10a may be given priority access to appointment slots, discounted premiums, and/or upgraded experiences based upon their loyalty status. FIG. 3 shows a table 300 of example loyalty benefits that a patient 10a may be afforded based on their loyalty level. In this example, a "diamond" level patient 10a is guaranteed a single occupancy room, among other benefits. A loyalty program may also help reduce reliance on payment options that a medical provider provides today for free, and help the medical provider to monetize components of payment services that the provider has not previously monetized. Moreover, by creating patient 10a loyalty levels, the medical provider may stratify who are their highest value patients and focus on amplifying their experiences. Furthermore, by creating a loyalty program, it is more likely that the patient 10a will stay with, and remain loyal to, the medical provider, and the medical provider may be able to capture more of their lifetime medical spending. In some examples, loyalty levels are based on, for example, total annual spend with a medical provider, being a member of the provider's health plan, spend using a branded credit card, donating annually to the provider's foundation, including the medical provider in their planned giving, etc.

Returning to FIG. 1, in the illustrated example, the computing device 30 also executes a rating module 130, which includes a trained rating ML model 132 and a rating UI module 134. The rating module 130 may be, or include, a portion of a memory unit (e.g., the memory hardware 34) configured to store software, and machine- or computer-readable instructions that, when executed by a processing unit (e.g., the data processing hardware 32), cause the rating module 130 to determine ratings information 136. In the illustrated example, the rating module 130 dynamically determines ratings information 136 using the trained rating ML model 132. The rating ML model 132 may be, or include, a portion of a memory unit (e.g., the memory hardware 34) configured to store software, and machine- or computer-readable instructions that, when executed by a processing unit (e.g., the data processing hardware 32, a GPU, a TPU, etc.), cause the rating ML model 132 to dynamically determine ratings.

In some implementations, another training process trains the rating ML model 132, using records 150*h* obtained from one or more electronic health record (EHR) systems associated with a plurality of medical providers, to determine one or more ratings for medical providers and/or medical resources. In some examples, the training process obtains current ratings information 136 for a plurality of medical providers and medical resources, and trains the rating ML model 132 using the current ratings information 136. Example EHR record data includes, but is not limited to, date, day-of-the-week, time-of-the-day, scheduled start time for overall service, actual start time for overall service, actual end time for overall service, total time for care for outpatient services, length of stay for inpatient services, scheduled start time for individual task, actual start time for individual task, actual end time for individual task, medications administered, daily living activities performed, services such as CT, MRI, etc., current procedural terminology (CPT) codes, Medicare severity diagnosis related group (MSDRG) codes, complexity of service, case mix index for inpatient services, procedure description, patient 10*a* satisfaction information, etc. In some examples, the patient 10*a* satisfaction information is obtained via text-based surveys. Here, pulling text-based survey information into the rating ML model 132 enables patients 10*a* to directly rate individual medical providers and medical resources, which is truly revolutionary in healthcare. Here, the EHR record data 150*h* includes EHR records for a plurality of medical providers and medical resources. In some examples, the training process updates the rating ML model 132 over time as new EHR records are available. Thus, each time new EHR records are available, the training process gains additional training data. Therefore, the ratings information 136 becomes a national database of every medical provider and medical resource in the country and their individual contributions to the overall health and well-being of their community.

In some examples, ratings information 136 generated by the ratings module 130 is used over time to track a medical provider's career, care, performance, etc. and/or to help identify areas where a medical provider may improve. For example, a nurse could see their entire performance across a 20-year career at 4 different employers. Showing that level of detail across all of patients 10*a* that a medical provider has cared for will elevate the level of care provided and thus improve patient 10*a* outcomes, reducing the cost of care, and saving countless lives.

In some examples, the training process trains the rating ML model to emphasize more recent data over older data. Thus, what has occurred in the most recent 90 days is more heavily weighted by the rating ML model 132, and older data is weighted less by the rating ML model 132. In some implementations, rating ML model 132 rates individuals based on a 1.0 scale. Results above a 1.0 indicates a star rating that is going to be 3+ stars, and results below 1.00 indicate a rating that's going to be below 3 stars. Here, a rating of three stars is considered average or acceptable performance. Here, the 5 star rating system was chosen to align with traditional performance rating systems that rely on a 5 point scale to grade an employee's contribution. It is structured similar to an evaluation on a 1 through 5 scale, where a 5 star rating represents exemplary performance. This rating system enables a medical provider or medical resource to distinguish themselves from their peer group in a positive or negative way. In some implementations, the ratings information 136 may be used to determine compensation and bonus structures. This will enable those performing at a high level to distinguish themselves and maximize their individual value.

When the EHR records 150*h* are taken from a plurality of different EHR record systems, the rating ML model 132 can, for example, analyze inpatient units across different hospitals and across different health systems. Being able to compare medical providers doing similar roles across differing sites and/or organizations will be a substantial advancement that exists nowhere in the healthcare ecosystem today. That is, medical providers can be analyzed on a truly national level, not just based on what's happening in a specific department or an individual hospital, but based on what's happening across, for example, an entire country. This will allow for more predictable patient 10*a* outcomes and reduced costs all while saving lives.

Figure 4:
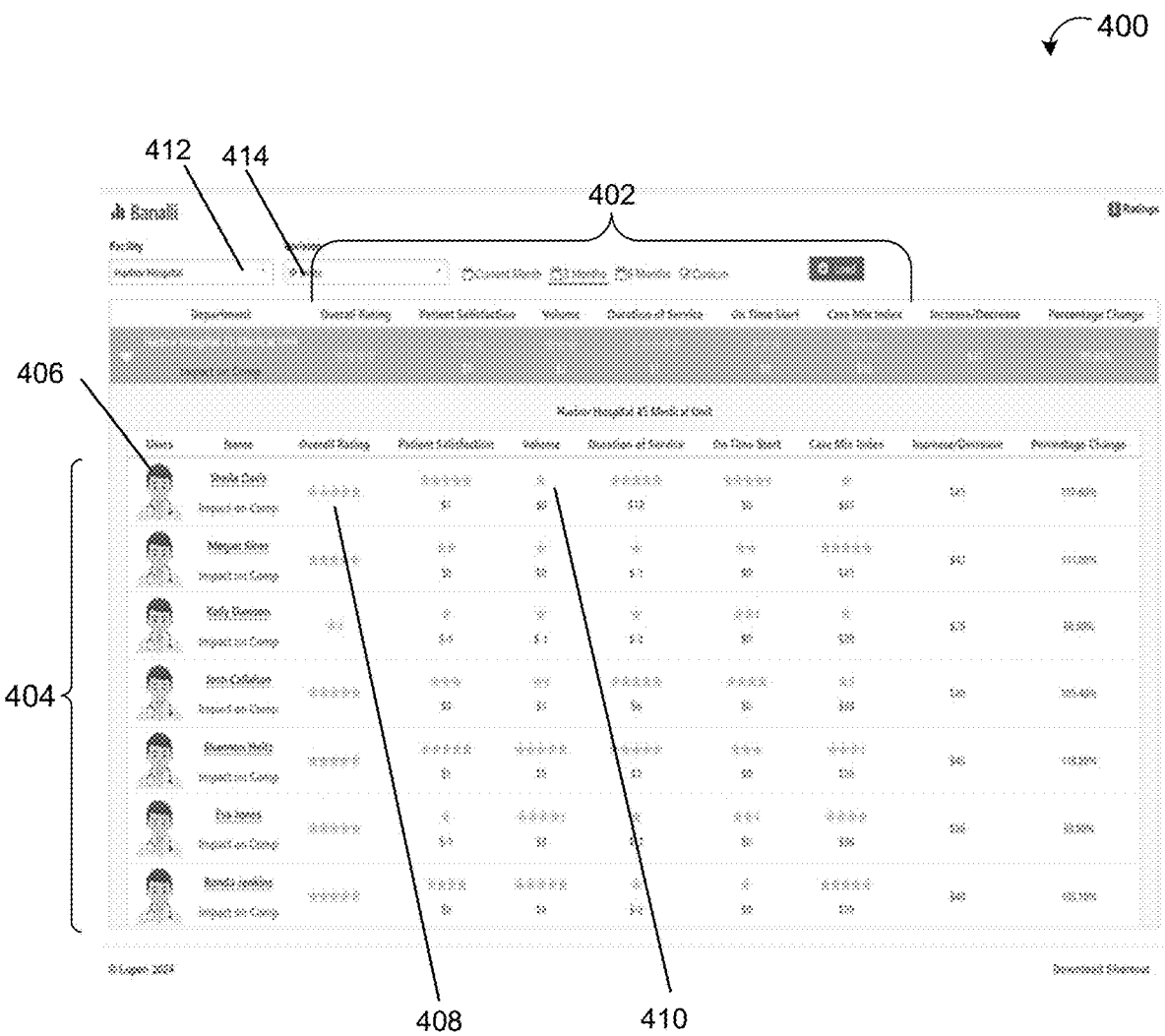
FIG. 4 illustrates an example ratings user interface for presenting provider ratings information.

FIG. 4 illustrates an example ratings UI 400 that may be provided by the rating UI module 134 for presenting ratings information. The ratings UI 400 may be, for example, a web-based interface. The example ratings UI 400 includes ratings in a plurality of categories 402 for a plurality of medical providers 404. Here, a rating is between one star and five stars, with five stars being the best rating possible. For example, Sheila Davis 406 has a five star overall rating 408, but only a one star volume rating 410 due to caring for a smaller number of patients. Here, the ratings are for a particular facility 412, a particular division 414. In this example, the ratings UI 400 includes drop-down boxes 412 and 414 that allow a user to select the particular facility 412, the particular division 414.

Returning to FIG. 1, in some examples, the load-leveling engine 120 and the rating module 130 may work cooperatively to determine appointment slot pricing. For example, if a patient 10*a* chooses a high demand appointment slot with a five star rated medical provider they will see a higher price for that appointment slot than if they choose a two star rated medical provider for the same appointment slot. The same applies to a less in demand appointment slot. In some implementations, a low demand appointment slot and a low rated medical provider may result in a negative price where the organization pays the patient 10*a* to take that time and staff member. On the backside, the patient 10*a* has the ability to rate that medical provider and directly contribute to their compensation and impacting their future ratings. This level of consumer involvement and empowerment does not exist anywhere in the healthcare landscape today.

In some implementations, the AI assisted dynamic medical appointment scheduling system 100 also includes a loyalty module 140. Today, healthcare is largely transaction based. A patient 10*a* has a need and then seeks out a medical provider to meet that need. Proximity and availability drive the majority of decisions about where to receive care. This costs medical providers an incredible amount of money to acquire patients 10*a* every time they have a need. The introduction of a loyalty program like infrastructure into healthcare will substantially change the dynamics that patients 10*a* and medical providers experience. However, the loyalty programs that exist in other industries such and the travel, hospitality, and retail environments will not adequately work for healthcare. Healthcare is a very fragmented ecosystem with each market containing a large number of organizations that are not always working together to advance the patient's interest.

With so many different medical providers, a patient 10*a* may have a disjointed and disconnected experience, at best. At worst, the patient 10*a* is receiving care and treatments that are working against one another. With all of these expenditures for care at the various medical providers, the patient 10*a* may not be receiving any benefit for being a loyal customer of a particular medical provider or group of medical providers. In fact, most healthcare medical providers have no way of knowing who their patients 10*a* are, how frequently they are visiting, or where they are meaningfully engaging with their patients 10*a*.

Advantageously, the loyalty module 140 can provide patients 10*a* with a loyalty platform that encourages their continued interaction with aligned medical providers. Through continued actions with aligned medical providers, a patient's care can be better coordinated, the patient 10*a* and medical providers can build a more sustainable relationship, and the patient 10*a* may build up loyalty reward points. The medical provider receives a higher-level assurance that the patient 10*a* will return to them when a need arises. The patient 10*a* receives personalized services and benefits for returning to a medical provider that is aligned with the loyalty platform. For example, a patient 10*a* who has earned a high status level may not have to wait to schedule an appointment, stand in line for a walk-in type service, or may receive a guaranteed single occupancy room when they need to stay in the hospital. Where a patient 10*a* who has earned a lower level of status may be able to access those services for a fee.

The iterations of service offerings, status levels, and earning opportunities across a group of independent organizations is what makes the loyalty module 140 different than other industry loyalty programs where they own most, if not all, of the service offerings. Here, the loyalty module 140 is designed as a white-label loyalty platform where each subset of medical provider will define the key components that are relevant to them and their constituents. In some examples, the design, layout, and functionality of a loyalty program UI will be standardized, but the patient 10*a* will see branding based upon their provider's program(s).

Figure 5:
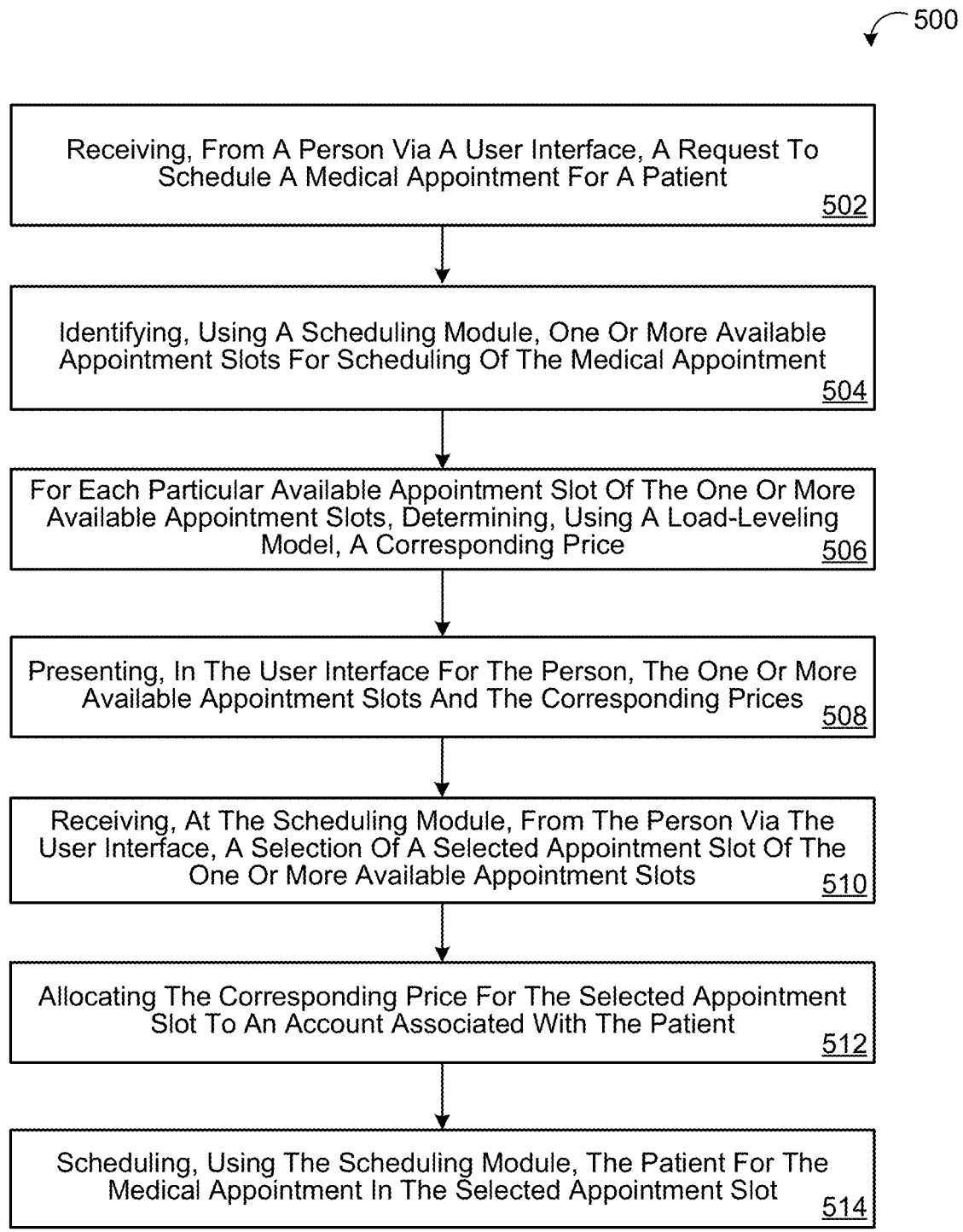
FIG. 5 is a flowchart of an example arrangement of operations for a computer-implemented method of AI assisted dynamic medical appointment scheduling.

FIG. 5 is a flowchart of an exemplary arrangement of operations for a computer-implemented method 500 for AI assisted dynamic medical appointment scheduling. The operations may be performed by data processing hardware 610 (FIG. 6) (e.g., the data processing hardware 22 of the user device 20 or the data processing hardware 32 of the computing device 30) based on executing instructions stored on memory hardware 620 (e.g., the memory hardware 24 of the user device 20 or the memory hardware 34 of the computing device 30).

At operation 502, the method 500 includes receiving, from a person 10 via the scheduling UI 200, a request to schedule a medical appointment for a patient 10*a*. The method 500 includes, at operation 504, identifying, using the scheduling module 110, one or more available appointment slots 128 for scheduling of the requested medical appointment. At operation 506, the method 500 includes, for each particular available appointment slot 128 of the one or more available appointment slots 128, determining, using the load-leveling ML model 122, a corresponding price 124. Here, a training process trains the load-leveling ML model 122 by obtaining training data includes historical data representing a plurality of past medical appointments, and training the load-leveling ML model 122, using the training data, to determine a corresponding price for a particular appointment slot to achieve a target utilization rate for the particular appointment slot.

At operation 508, the method 500 includes presenting, to the person 10 in the scheduling UI 200, the one or more available appointment slots 128 and the corresponding prices 124. The method 500 includes, at operation 510, receiving, at the scheduling module 110, a selection of a selected appointment slot 128 of the one or more available appointment slots 128. At operation 510, the method 500 includes allocating the corresponding prices 124 for the selected appointment slot 128 to an account associated with the patient 10*a*. At operation 510, the method 500 includes scheduling, using the scheduling module 110, the patient 10*a* for the medical appointment in the selected appointment slot 128 with the medical provider. In some examples, the premium is non-refundable even if the patient 10*a* does not show up for the appointment or cancels/changes the appointment.

Figure 6:
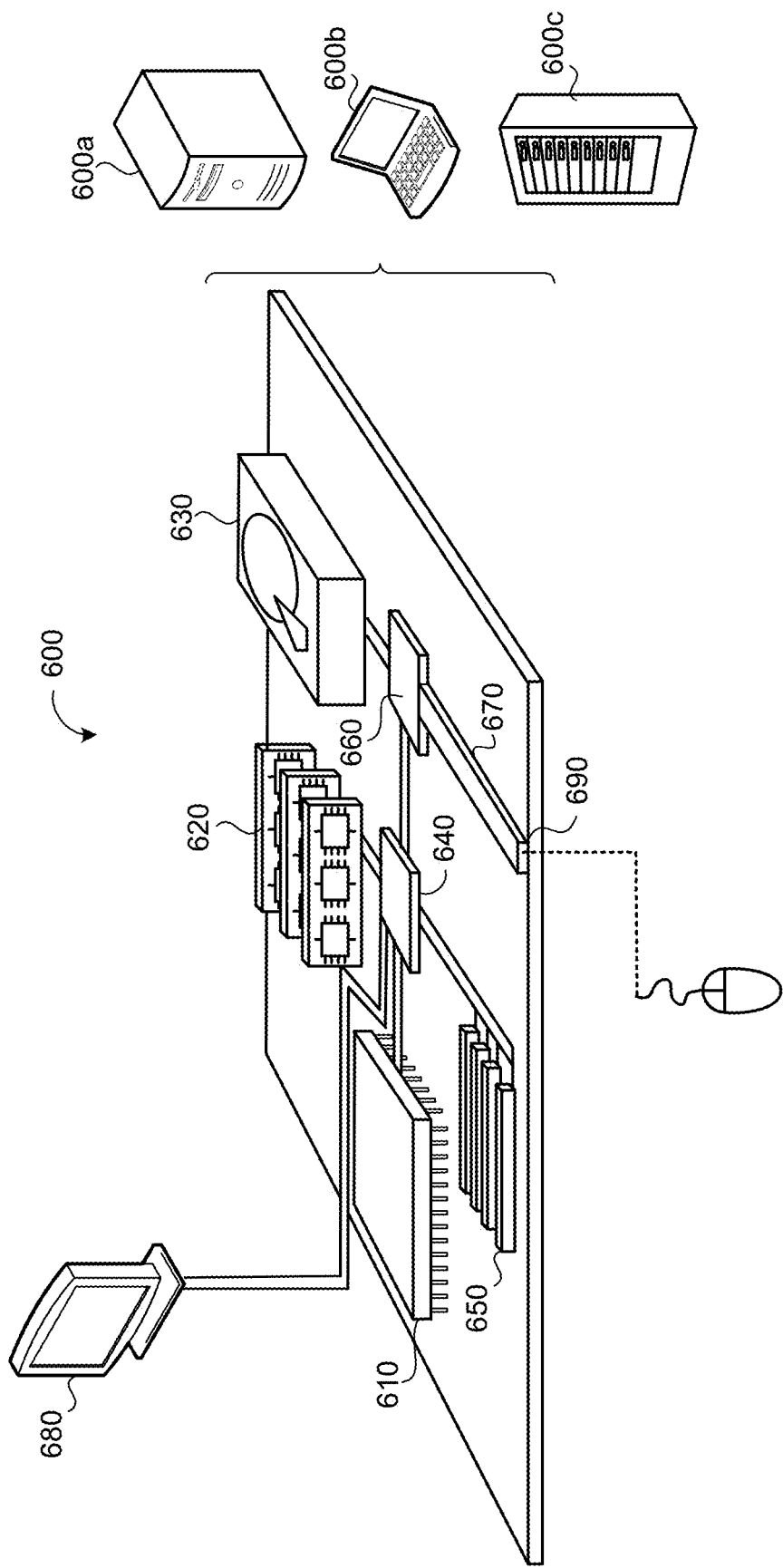
FIG. 6 is a schematic view of an example computing device that may be used to implement the systems and methods described herein.

FIG. 6 is schematic view of an example computing device 600 that may be used to implement the systems and methods described in this document. The computing device 600 is intended to represent various forms of digital computers, such as laptops, desktops, workstations, personal digital assistants, servers, blade servers, mainframes, and other appropriate computers. The components shown here, their connections and relationships, and their functions, are meant to be exemplary only, and are not meant to limit implementations of the inventions described and/or claimed in this document.

The computing device 600 includes a processor 610 (i.e., data processing hardware) that can be used to implement the data processing hardware 22 and/or 32, memory 620 (i.e., memory hardware) that can be used to implement the memory hardware 24 and/or 34, a storage device 630 (i.e., memory hardware) that can be used to implement the memory hardware 24, 34 and/or the datastores 150, a high-speed interface/controller 640 connecting to the memory 620 and high-speed expansion ports 650, and a low speed interface/controller 660 connecting to a low speed bus 670 and a storage device 630. Each of the components 610, 620, 630, 640, 650, and 660, are interconnected using various busses, and may be mounted on a common motherboard or in other manners as appropriate. The processor 610 can process instructions for execution within the computing device 600, including instructions stored in the memory 620 or on the storage device 630 to display graphical information for a graphical user interface (GUI) on an external input/output device, such as display 680 coupled to high speed interface 640. In other implementations, multiple processors and/or multiple buses may be used, as appropriate, along with multiple memories and types of memory. Also, multiple computing devices 600 may be connected, with each device providing portions of the necessary operations (e.g., as a server bank, a group of blade servers, or a multi-processor system).

The memory 620 stores information non-transitorily within the computing device 600. The memory 620 may be a computer-readable medium, a volatile memory unit(s), or non-volatile memory unit(s). The non-transitory memory 620 may be physical devices used to store programs (e.g., sequences of instructions) or data (e.g., program state information) on a temporary or permanent basis for use by the computing device 600. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

The storage device 630 is capable of providing mass storage for the computing device 600. In some implementations, the storage device 630 is a computer-readable medium. In various different implementations, the storage device 630 may be a floppy disk device, a hard disk device, an optical disk device, or a tape device, a flash memory or other similar solid state memory device, or an array of devices, including devices in a storage area network or other configurations. In additional implementations, a computer program product is tangibly embodied in an information carrier. The computer program product contains instructions that, when executed, perform one or more methods, such as those described above. The information carrier is a computer- or machine-readable medium, such as the memory 620, the storage device 630, or memory on processor 610.

The high speed controller 640 manages bandwidth-intensive operations for the computing device 600, while the low speed controller 660 manages lower bandwidth-intensive operations. Such allocation of duties is exemplary only. In some implementations, the high-speed controller 640 is coupled to the memory 620, the display 680 (e.g., through a graphics processor or accelerator), and to the high-speed expansion ports 650, which may accept various expansion cards (not shown). In some implementations, the low-speed controller 660 is coupled to the storage device 630 and a low-speed expansion port 690. The low-speed expansion port 690, which may include various communication ports (e.g., USB, Bluetooth, Ethernet, wireless Ethernet), may be coupled to one or more input/output devices, such as a keyboard, a pointing device, a scanner, or a networking device such as a switch or router, e.g., through a network adapter.

The computing device 600 may be implemented in a number of different forms, as shown in the figure. For example, it may be implemented as a standard server 600*a* or multiple times in a group of such servers 600*a*, as a laptop computer 600*b*, or as part of a rack server system 600*c*.

Various implementations of the systems and techniques described herein can be realized in digital electronic and/or optical circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

A software application (i.e., a software resource) may refer to computer software that causes a computing device to perform a task. In some examples, a software application may be referred to as an "application," an "app," or a "program." Example applications include, but are not limited to, system diagnostic applications, system management applications, system maintenance applications, word processing applications, spreadsheet applications, messaging applications, media streaming applications, social networking applications, and gaming applications.

These computer programs (also known as programs, software, software applications, or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, non-transitory computer readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

The processes and logic flows described in this specification can be performed by one or more programmable processors, also referred to as data processing hardware, executing one or more computer programs to perform functions by operating on input data and generating output. The processes and logic flows can also be performed by special purpose logic circuitry, e.g., an FPGA (field programmable gate array) or an ASIC (application specific integrated circuit). Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Unless expressly stated to the contrary, the phrase "at least one of A, B, or C" is intended to refer to any combination or subset of A, B, C such as: (1) at least one A alone; (2) at least one B alone; (3) at least one C alone; (4) at least one A with at least one B; (5) at least one A with at least one C; (6) at least one B with at least one C; and (7) at least one A with at least one B and at least one C. Moreover, unless expressly stated to the contrary, the phrase "at least one of A, B, and C" is intended to refer to any combination or subset of A, B, C such as: (1) at least one A alone; (2) at least one B alone; (3) at least one C alone; (4) at least one A with at least one B; (5) at least one A with at least one C; (6) at least one B with at least one C; and (7) at least one A with at least one B and at least one C. Furthermore, unless expressly stated to the contrary, "A or B" is intended to refer to any combination of A and B, such as: (1) A alone; (2) B alone; and (3) A and B.

A number of implementations have been described. Nevertheless, it will be understood that various modifications may be made without departing from the spirit and scope of the disclosure. Accordingly, other implementations are within the scope of the following claims.

What is claimed is:

1. A computer-implemented method executed on data processing hardware that causes the data processing hardware to perform operations comprising:
   receiving, from a person via a user interface, a request to schedule a medical appointment for a patient;
   identifying, using a scheduling module, a schedule comprising one or more available appointment slots for scheduling of the medical appointment;
   determining, for each particular available appointment slot of the one or more available appointment slots, a corresponding price, wherein determining the corresponding prices comprises executing, on the data processing hardware, instructions that cause the data processing hardware to execute a trained load-leveling machine-learning (ML) model that:
      inputs the schedule; and
      determines, based on the inputted schedule, the corresponding price for each of the one or more available appointment slots of the inputted schedule, and wherein a training process trains the load-leveling ML model by:
         obtaining first training data comprising first historical data representing a first plurality of past medical appointments;
         training, based on the first training data, the load-leveling ML model in a first stage to teach the load-leveling ML model to determine a corresponding price for each particular appointment slot of an inputted schedule to achieve a target utilization rate for each particular appointment slot of the inputted schedule, the target utilization rate representing a percentage of time that an appointment is scheduled in the particular appointment slot;
         obtaining second training data comprising second historical data representing a second plurality of past appointments scheduled based on prices determined using the load-leveling ML model; and
         training, based on the second training data, the load-leveling ML model in a second stage to teach the load-leveling ML model to determine a corresponding price for each particular appointment slot of an inputted schedule to achieve a target utilization rate;
   presenting, in the user interface for the person, the one or more available appointment slots and the corresponding prices;
   receiving, at the scheduling module, from the person via the user interface, a selection of a selected appointment slot of the one or more available appointment slots;
   allocating the corresponding price for the selected appointment slot to an account associated with the patient; and
   scheduling, using the scheduling module, the patient for the medical appointment in the selected appointment slot.

2. The method of claim 1, wherein:
   at least one of the available appointment slots for scheduling of the requested medical appointment comprises corresponding available appointments slots for one or more medical providers that can perform the medical appointment;
   determining the corresponding price for the at least one of the available appointment slots comprises determining a corresponding price for each of the one or more medical providers for the at least one the available appointment slots; and
   presenting, in the user interface for the person, the one or more available appointment slots and the corresponding prices comprises presenting the corresponding available appointment slots for the one or more medical providers and the corresponding price for each of the one or more medical providers for the at least one of the available appointment slots.

3. The method of claim 1, wherein the historical data comprises, for each past appointment of the plurality of past appointments, at least one of:
   a date;
   a day of a week;
   a day of a month;
   a month of a year;
   a scheduled start time;
   an actual start time;
   a duration;
   a current procedural terminology (CPT) code;
   a procedure description;
   a practitioner identifier;
   an equipment identifier;
   a location identifier;
   a room identifier; or
   a surcharge amount.

4. The method of claim 1, wherein the historical data represents past appointments for a plurality of medical providers.

5. The method of claim 1, wherein the training process trains the load-leveling model to increase a revenue associated with a particular appointment slot.

6. The method of claim 1, wherein the training process trains the load-leveling model to determine the corresponding price based on loyalty program information for the patient.

7. The method of claim 1, wherein allocating the corresponding price for the selected appointment slot to the account associated with the patient comprises deducting points from a loyalty program account associated with the patient.

8. The method of claim 1, wherein the training process trains the load-leveling model to determine the corresponding price for an available appointment slot based on a rating for a medical provider.

9. The method of claim 8, wherein the rating for the medical provider comprises at least one of:
an overall rating;
a patient satisfaction score;
a volume;
a duration of service rating;
an on-time start rating; or
a case mix rating.

10. The method of claim 8, wherein the operations further comprise:
determining, using a ratings ML model, the rating for the medical provider,
wherein a second training process trains the rating ML model by:
obtaining records from an electronic health records (EHR) system associated with a plurality of medical providers; and
training the rating ML model, using the records, to determine one or more ratings for each of the plurality of medical providers.

11. The method of claim 10, wherein the second training process:
obtains current ratings information for each of the plurality of medical providers; and
trains the rating ML model, using the records and the current ratings information, to determine the one or more ratings for each of the plurality of medical providers.

12. The method of claim 1, wherein presenting, in the user interface for the person, the one or more available appointment slots and the corresponding prices comprises presenting a schedule, wherein the schedule comprises each available appointment slot the corresponding price.

13. The method of claim 1, wherein the prices comprise a surcharge that is charged to the patient, the surcharge is separate from an amount charged to an insurer for the medical appointment.

14. A system comprising:
data processing hardware; and
memory hardware in communication with the data processing hardware, the memory hardware storing instructions that, when executed on the data processing hardware, cause the data processing hardware to perform operations comprising:
receiving, from a person via a user interface, a request to schedule a medical appointment for a patient;
identifying, using a scheduling module, a schedule comprising one or more available appointment slots for scheduling of the medical appointment;
determining, for each particular available appointment slot of the one or more available appointment slots, a corresponding price, wherein determining the corresponding prices comprises executing, on the data processing hardware, instructions that cause the data processing hardware to execute a trained load-leveling machine-learning (ML) model that:
inputs the schedule; and
determines, based on the inputted schedule, the corresponding price for each of the one or more available appointment slots of the inputted schedule, and wherein a training process trains the load-leveling ML model by:
obtaining first training data comprising first historical data representing a first plurality of past medical appointments;
training, based on the first training data, the load-leveling ML model in a first stage to teach the load-leveling ML model to determine a corresponding price for each particular appointment slot of an inputted schedule to achieve a target utilization rate for each particular appointment slot of the inputted schedule, the target utilization rate representing a percentage of time that an appointment is scheduled in the particular appointment slot;
obtaining second training data comprising second historical data representing a second plurality of past appointments scheduled based on prices determined using the load-leveling ML model; and
training, based on the second training data, the load-leveling ML model in a second stage to teach the load-leveling ML model to determine a corresponding price for each particular appointment slot of an inputted schedule to achieve a target utilization rate;
presenting, in the user interface for the person, the one or more available appointment slots and the corresponding prices;
receiving, at the scheduling module, from the person via the user interface, a selection of a selected appointment slot of the one or more available appointment slots;
allocating the corresponding price for the selected appointment slot to an account associated with the patient; and
scheduling, using the scheduling module, the patient for the medical appointment in the selected appointment slot.

15. The system of claim 14, wherein:
at least one of the available appointment slots for scheduling of the requested medical appointment comprises corresponding available appointments slots for one or more medical providers that can perform the medical appointment;
determining the corresponding price for the at least one of the available appointment slots comprises determining a corresponding price for each of the one or more medical providers for the at least one the available appointment slots; and
presenting, in the user interface for the person, the one or more available appointment slots and the corresponding prices comprises presenting the corresponding available appointment slots for the one or more medical providers and the corresponding price for each of the one or more medical providers for the at least one of the available appointment slots.

16. The system of claim 14, wherein the historical data comprises, for each past appointment of the plurality of past appointments, at least one of:
a date;
a day of a week;
a day of a month;
a month of a year;
a scheduled start time;
an actual start time;
a duration;

a current procedural terminology (CPT) code;
a procedure description;
a practitioner identifier;
an equipment identifier;
a location identifier;
a room identifier; or
a surcharge amount.

17. The system of claim 14, wherein the historical data represents past appointments for a plurality of medical providers.

18. The system of claim 14, wherein the training process trains the load-leveling model to increase a revenue associated with a particular appointment slot.

19. The system of claim 14, wherein the training process trains the load-leveling model to determine the corresponding price based on loyalty program information for the patient.

20. The system of claim 14, wherein allocating the corresponding price for the selected appointment slot to the account associated with the patient comprises deducting points from a loyalty program account associated with the patient.

21. The system of claim 14, wherein the training process trains the load-leveling model to determine the corresponding price for an available appointment slot based on a rating for a medical provider.

22. The system of claim 21, wherein the rating for the medical provider comprises at least one of:
an overall rating;
a patient satisfaction score;
a volume;
a duration of service rating;
an on-time start rating; or
a case mix rating.

23. The system of claim 21, wherein the operations further comprise:
determining, using a ratings ML model, the rating for the medical provider,
wherein a second training process trains the rating ML model by:
obtaining records from an electronic health records (EHR) system associated with a plurality of medical providers; and
training the rating ML model, using the records, to determine one or more ratings for each of the plurality of medical providers.

24. The system of claim 23, wherein the second training process:
obtains current ratings information for each of the plurality of medical providers; and
trains the rating ML model, using the records and the current ratings information, to determine the one or more ratings for each of the plurality of medical providers.

25. The system of claim 14, wherein presenting, in the user interface for the person, the one or more available appointment slots and the corresponding prices comprises presenting a schedule, wherein the schedule comprises each available appointment slot the corresponding price.

26. The system of claim 14, wherein the prices comprise a surcharge that is charged to the patient, the surcharge is separate from an amount charged to an insurer for the medical appointment.

* * * * *